(12) United States Patent
Müller et al.

(10) Patent No.: US 6,992,182 B1
(45) Date of Patent: Jan. 31, 2006

(54) METHOD FOR ISOLATING DNA FROM BIOLOGICAL MATERIALS

(75) Inventors: Oliver Müller, Dortmund (DE); Markus Sprenger-Haussels, Solingen (DE); Helge Bastian, Düsseldorf-Benrath (DE); Stefanie Vollert, Hofheim-Lorsbach (DE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 09/889,093

(22) PCT Filed: Jan. 5, 2000

(86) PCT No.: PCT/EP00/00052

§ 371 (c)(1),
(2), (4) Date: Oct. 15, 2001

(87) PCT Pub. No.: WO00/42177

PCT Pub. Date: Jul. 20, 2000

(30) Foreign Application Priority Data

Jan. 11, 1999 (DE) ................................ 199 00 638

(51) Int. Cl.
*C12P 19/34* (2006.01)
*C07H 21/00* (2006.01)
*C07H 21/02* (2006.01)
*C07H 21/04* (2006.01)

(52) U.S. Cl. .................. 536/25.41; 536/25.4; 435/91.5

(58) Field of Classification Search ................ 435/91.5; 536/25.4, 25.41, 18.5, 22.1, 23.1, 24.31

See application file for complete search history.

(56) References Cited

U.S. PATENT DOCUMENTS 5,817,798 A   10/1998   Gundling
6,084,091 A * 7/2000   Muller et al.

FOREIGN PATENT DOCUMENTS

WO    WO 97/07239       2/1997
WO    WO 97/ 07239   *  2/1997

OTHER PUBLICATIONS

Wan et al. A modified hot borate method significantly enhances the yield of high-quality RNA from cotton Analytical Biochemist vol. 223 pp. 7-12 1994.*
Bretagne et al., 1993. Parasitology 106(2): 193-199.
Deuter et al., 1995. Nucleic Acids Research 23(18): 3800-3801.
Flagstad et al., 1999. Molecular Ecology 8(5): 879-883.
Gouvea et al., 1997. Journal of Virological Methods 69(1-2): 53-61.
Central Patents Index, Basic Abstracts Journal, Derwent Publications Ltd., London, 1979, Nr. 69612 B/38 zu: SU 638599.
Sivolap et al., Chemical Abstracts 117 (1992) 206001u.
Chung et al., Chemical Abstracts 127 (1997) 146699x.

* cited by examiner

*Primary Examiner*—James Ketter
*Assistant Examiner*—Konstantina M. Katcheves
(74) *Attorney, Agent, or Firm*—Yankwich & Associates, P.C.; Leon R. Yankwich; Michael R. Wesolowski

(57) ABSTRACT

The invention relates to a method for the stabilization, purification or/and isolation of nucleic acids from biological materials, in particular stool samples which may contain contaminations and interfering substances. Furthermore, a reagent kit suitable for carrying out the method of the invention is described.

Figure 1:
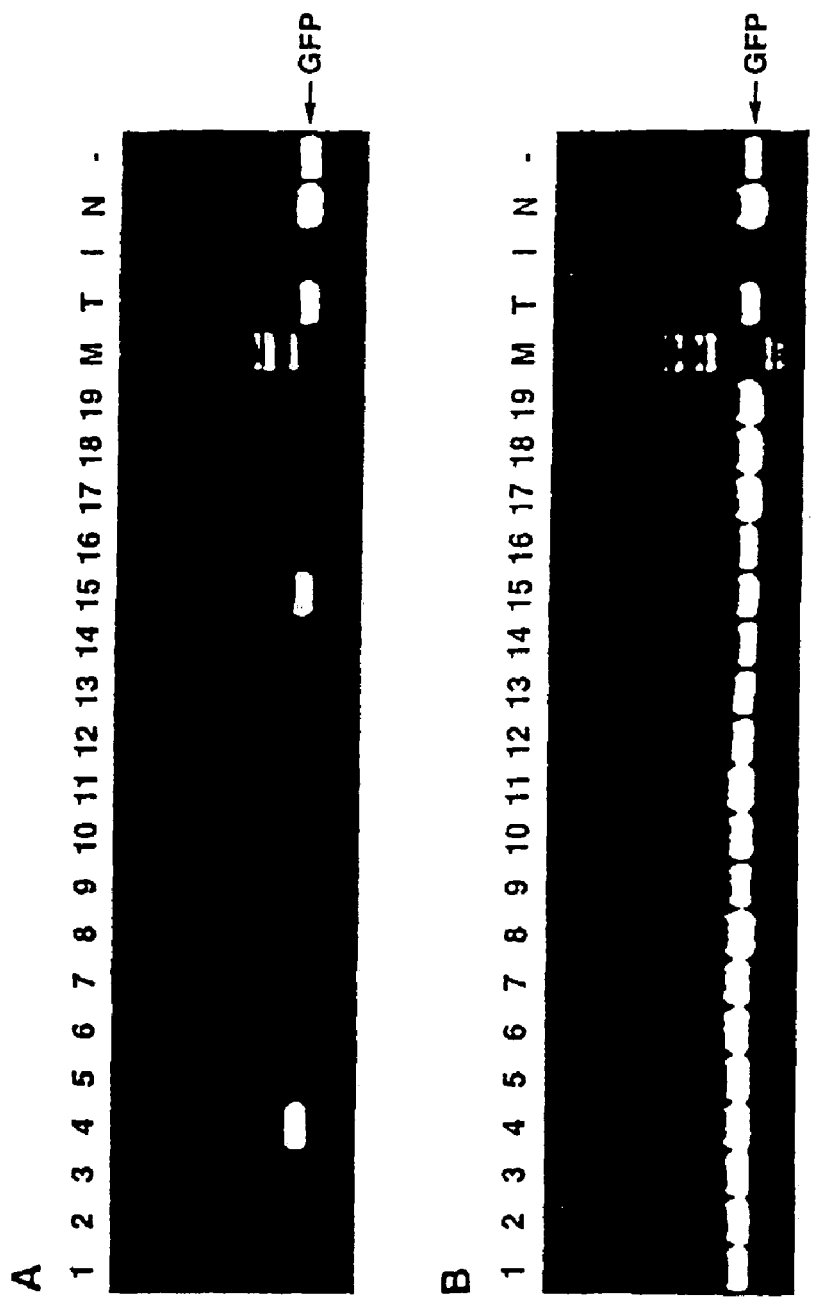

13 Claims, 1 Drawing Sheet

METHOD FOR ISOLATING DNA FROM BIOLOGICAL MATERIALS

CROSS-REFERENCE TO RELATED APPLICATIONS

This application is a national stage application of PCT/EP00/00052, filed 5 Jan. 2000, which claims priority to German application DE 199 00 638.5, filed 11 Jan. 1999, the entirety of which is hereby incorporated by reference.

DESCRIPTION

The invention relates to a method for the stabilization, purification or/and isolation of nucleic acids from biological materials, in particular stool samples which may contain contaminations and inhibitors or interfering substances. Furthermore, a reagent kit suitable for carrying out the method of the invention is described.

Numerous examples from various research areas verify the importance of analyzing nucleic acids from biological materials contaminated with substances which damage nucleic acids during storage and hinder an enzymatic manipulation of the nucleic acids, for example by amplification. It is therefore important for the usability of the nucleic acids contained in the biological materials for further analyses that said substances are present only at very low concentrations or are completely removed from the sample.

The analysis of nucleic acids from fecal samples is of particular importance. An important medical application is the detection of tumor-specific modifications of nuclear human DNA from stools, which may serve as parameters in the early diagnosis of tumors of the digestive tract. Likewise, the detection of bacterial and viral infectious pathogens from stool samples by nucleic acid-based assay methods becomes increasingly important.

The application of a combination of various purification steps such as protease treatment, phenol/chloroform extraction, binding of nucleic acids to silica in the presence of chaotropic salts, gel filtration, anion exchange chromatography and the use of cationic detergents is well known for the purification of nucleic acids from stool samples. However, the nucleic acids isolated from stool samples using said methods are generally unstable and often cause problems in subsequent enzymatic reactions such as, for example, PCR. The reason for this are substances which are isolated together with the nucleic acid and which damage said nucleic acid and also inhibit enzymatic reactions. Inhibitor classes contained in stools, where known, are hemoglobin and its metabolites, bile acids and bile acid derivatives and also polysaccharides.

PCT/EP/96/03595 describes a method for purifying, stabilizing or/and isolating nucleic acids from biological materials, in particular feces, in which an adsorption matrix for binding contaminations is added to a nucleic acid-containing sample from biological materials. The adsorption matrix used is preferably carbohydrate-based, for example starch, cellulose, glycogen or/and other biogenic or nonbiogenic carbohydrates or mixtures thereof, with flours made of cereals, peas, corn, potatoes or components thereof or mixtures being preferred. Mixtures of purified carbohydrates or/and flours, in particular mixtures of cellulose and potato flour, have proved particularly suitable for purifying nucleic acids from stool samples.

In some cases however, the nucleic acid-damaging substances and PCR inhibitors are not completely removed when using the method described in PCT/EP96/03595. In the case of a—variable—proportion of inhibitory stool samples, the enzymatic treatment of the nucleic acids following purification using the standard protocol is not possible.

It was therefore an object of the present invention to provide a method for purifying nucleic acids, which removes at least some of the disadvantages of the prior art and which in particular makes it possible to reproducibly purify nucleic acids from "inhibitory samples".

Surprisingly, it was found that purification of nucleic acids can be improved even from inhibitory samples when taking one or more of the measures mentioned below:

(a) using an extraction buffer having an acidic to neutral pH,
(b) using an extraction buffer having a high salt content and
(c) using an extraction buffer containing a phenol-neutralizing substance.

The invention therefore relates to a method for the purification, stabilization or/and isolation of nucleic acids from biological materials, in which an extraction buffer and an adsorption matrix for binding contaminations are added to the nucleic acid-containing sample and the nucleic acids are subsequently removed from the adsorption matrix, and contaminations bound thereto, the extraction buffer containing (a) a pH in the range from 2–8,
(b) a salt concentration of at least 100 mM or/and
(c) a phenol-neutralizing substance.

In a first embodiment, the buffer has a pH in the range from 2 to 8, preferably from 3 to 7 and particularly preferably from 4 to 6.5. The use of acetate buffers, for example Na acetate, has proved beneficial here. However, it is also possible to use other buffers, for example phosphate buffers or citrate buffers.

According to a second embodiment, the extraction buffer contains a salt concentration of at least 100 mM, preferably of at least 200 mM up to the maximum solubility of the salt used in each case. The preferred salt used is an alkali metal halide, for example NaCl or KCl or mixtures thereof.

According to a third embodiment, the buffer contains at least one phenol-neutralizing substance. Preferred examples of substances which can neutralize phenols are polyvinylpyrrolidone (PVP) of various polymerization grades, e.g. PVP-10, reducing agents, e.g. thiol reagents such as β-mercaptoethanol or dithiothreitol or borates. Particular preference is given to using polyvinylpyrrolidone at a concentration of at least 0.5% (w/w) up to the solubility limit.

Furthermore, the extraction buffers suitable for the method of the invention preferably contain a chelator such as EDTA, for example, or/and a detergent, for example an ionic detergent such as SDS. The chelator is present preferably at a concentration of 1 to 200 mM. The detergent concentration is preferably from 0.1 to 5% (w/w).

The adsorption matrix is such that it can, in combination with the extraction buffer, remove or neutralize contaminations which lead to damage of nucleic acids or/and prevent enzymatic reactions from being carried out or/and inhibit enzymatic reactions, examples of which are degradation products of hemoglobin, for example bilirubin and its degradation products, bile acids or salts thereof or their degradation products or/and polysaccharides and polyphenols, in particular of plant origin. Preference is given to using an insoluble adsorption matrix.

With respect to the suitable adsorption matrices, reference is made to the application PCT/EP96/0359. Particular preference is given to using carbohydrate-based adsorption matrices, for example flours made of cereals, corn, peas, soybean and in particular of potatoes or components thereof or mixtures thereof. Particular preference is given to mixtures of flours with other carbohydrates, for example purified carbohydrates such as cellulose.

The amount in which the adsorption matrix is added to the sample essentially depends on the sample composition. The adsorption matrix may be employed, for example, in a proportion by weight of from 0.05:1 to 100:1, in particular from 0.1:1 to 10:1, based on the sample.

The nucleic acid-containing sample is taken from biological materials which contain nucleic acid-degrading or enzymatic reaction-inhibiting contamination. The preferred source of the sample is feces. However, said sample may also be taken from other sources, e.g. tissues of all kinds, bone marrow, human and animal body fluids such as blood, serum, plasma, urine, sperm, CSF, sputum and swabs, plants, parts and extracts of plants, e.g. saps, fungi, microorganisms such as bacteria, fossilized or mummified samples, soil samples, sludge, waste waters and food.

Preferably, the sample is taken up in extraction buffer prior to adding the adsorption matrix and is preincubated for a period desired in each case. On the other hand, it is also possible to add sample, extraction buffer and adsorption matrix together at the same time. The extraction buffer is preferably used in a proportion by weight of at least 0.1:1, in particular of from 0.5:1 to 50:1, based on the sample. The sample may be incubated in the extraction buffer at room temperature and the incubation preferably includes a homogenization step, for example by vortexing.

In an embodiment of the invention, the incubation may be carried out under conditions which are beneficial for a release of the nucleic acids from the sample material. Such incubation conditions are used in particular if nucleic acids from materials "difficult" to break down, for example cells such as bacteria or parasites or viruses for example, are to be detected. In this case, the release of the nucleic acids during the incubation can be improved by chemical, thermal or/and enzymatic treatment, as a result of which a higher yield of nucleic acids is obtained from the sample material, both regarding total DNA and, specifically, regarding the DNA to be detected. It is preferred here to raise the temperature, for example to $\geq 50°$ C., in particular to $\geq 70°$ C.

If, on the other hand, nucleic acids from materials easy to break down, sensitive cells such as human cells for example, are to be determined, the incubation may also be carried out at a reduced temperature, for example $\leq 10°$ C., in particular $\leq 4°$ C., in order to avoid or restrict in this way the undesired release of other nucleic acids in the sample.

After addition of the adsorption matrix, the sample is further incubated. This incubation, too, may be carried out at room temperature, at a reduced temperature or at conditions beneficial to the release of nucleic acids, depending on the requirement.

After the incubation, the adsorption matrix can be removed from the sample by centrifugation, for example. Alternatively, the adsorption matrix may be added directly to the sample, for example in the case of liquid biological samples. Furthermore, it is possible to direct the sample over an adsorption matrix by centrifugation, application of reduced pressure or/and by means of gravity, with the adsorption matrix then being preferably present in a column.

The treatment with extraction buffer and adsorption matrix leads to a significant increase in stability of the nucleic acids contained in the sample and to a better reproducibility of the subsequent isolation of the nucleic acids. This is true in particular if the isolation is followed by enzymatic manipulation of the nucleic acids, for example an amplification or/and a restriction cleavage. Particular preference is given to carrying out the amplification, for example by PCR (polymerase chain reaction), LCR (ligase chain reaction), NASBA (nucleic acid base-specific amplification) or 3SR (self-sustained sequence replication).

As already mentioned in PCT/EP96/03595, a particularly preferred aspect of the present invention is the analysis, detection or isolation of nucleic acids, in particular DNA, from stool samples. The method of the invention makes it possible to obtain clean and amplifiable nucleic acids from fecal samples, which can be used for detecting mutations, in particular tumor-specific DNA mutations.

The present invention further relates to a reagent kit for stabilizing and purifying nucleic acids from biological materials, comprising:

(a) an extraction buffer as described above which is suitable for taking up a nucleic acid-containing sample, and (b) an adsorption matrix for binding contaminations of the biological materials.

The adsorption matrix may be present packaged in portions, for example packed in a column such as, for example, a minicolumn which can be centrifuged. The buffer may be present in a ready-to-use form, as concentrate or as lyophilizate.

The reagent kit preferably contains additional means for purifying nucleic acids, which include, for example, mineral or/and organic support materials and, where appropriate, solutions, auxiliary substances or/and accessories. Mineral components of support materials may be, for example porous or nonporous metal oxides or metal mixed oxides, for example aluminum oxide, titanium dioxide or zirconium dioxide, silica gels, glass-based materials, for example modified or unmodified glass particles or glass powder, quartz, zeolites or mixtures of one or more of the above-mentioned substances. On the other hand, the support may also contain organic components which are selected from, for example, latex particles optionally modified with functional groups, synthetic polymers such as, for example, polyethylene, polypropylene, polyvinylidene fluoride, in particular ultra high molecular weight polyethylene or HD polyethylene, or mixtures of one or more of the above-mentioned substances.

The support may be present, for example, in the form of particles having an average size of from 0.1 $\mu$m to 100 $\mu$m. When using a porous support, an average pore size of from 2 $\mu$m to 100 $\mu$m is preferred. The support may be present, for example, in the form of loose beds of particles, filtering layers, for example made of glass, quartz or ceramic, membranes, for example membranes in which a silica gel has been arranged, fibers or tissues of mineral support materials, such as, for example quartz or glass wool and also in the form of latices or frit materials of synthetic polymers.

In addition, the reagent kit of the invention may also contain auxiliary substances such as enzymes and other means for manipulation of nucleic acids, for example at least one amplification primer and enzymes suitable for amplification of nucleic acids, for example a nucleic acid polymerase or/and at least one restriction endonuclease.

The primers for amplification of nucleic acids are expediently derived from the genes to be analyzed, i.e. for example from oncogenes, tumor suppressor genes or/and microsatellite sections. Enzymes suitable for amplification of nucleic acids and restriction endonucleases are well known and commercially available.

In addition, the following figures and examples are intended to illustrate the present invention. In the figures:

FIG. 1: shows the amplificability of DNA in inhibitory stool samples using an extraction buffer of the prior art (FIG. 1a) and an extraction buffer of the invention (FIG. 1b).

EXAMPLE 1

Analysis of DNA from Stool Samples

DNA was purified from stool samples using an adsorption matrix made of cellulose and potato flour and then amplified by means of PCR.

Human stool samples were collected, frozen and stored at −80° C. 200 mg of stools were introduced into a 2 ml microcentrifuge vessel and stored on ice. The stool sample was then taken up in 600 µl of extraction buffer and the mixture was homogenized by vortexing for 1 min.

The potato flour and cellulose-based adsorption matrix (200 mg) was taken up in 300 µl of extraction buffer and resuspended by vortexing. The matrix suspension was then added to the stool homogenate and subjected to vortexing for 1 min.

The sample was centrifuged for 5 min in order to precipitate stool particles, the adsorption matrix and other contaminations. The supernatant was transferred to a new microcentrifuge vessel and centrifuged for a further 5 min.

The DNA contained in 600 µl of the supernatant was further purified with the aid of reagents and centrifugation columns, as described below. After proteinase K treatment, the nucleic acids were bound to a silica gel membrane of a centrifugation column in the presence of chaotropic salts and eluted after repeated washing steps.

A template (a DNA coding for GFP (green fluorescence protein)) and the other components (primers, polymerase, nucleotides, buffers) necessary for its amplification were added to the DNA eluates. The final concentration of the DNA eluates in the PCR mixture was 10% (v/v).

DNA isolates from inhibitory stool samples of a total of 19 individuals were tested for amplificability by means of PCR (lanes 1 to 19 in FIGS. 1a and b). After PCR, the mixtures were fractionated by gel electrophoresis and the amplification products (expected length 771 bp) were visualized by ethidium bromide staining.

A DNA length marker (M; 1 kB Marker, Gibco BRL, Bethesda Md.) was applied to the gel as a reference. Controls added to the GFP-PCR mixture instead of the DNA eluates were Tris buffer (T), a highly inhibitory stool DNA (I) or a non-inhibitory stool DNA (N). Moreover, in a control reaction GFP was amplified without any additions (−).

In the case of inhibitory stool samples, it was often impossible to obtain an amplification product when using the stool-dissolving buffer (500 mM Tris-HCl pH 9.0, 50 mM EDTA, 10 mM NaCl) used in PCT/EP96/03595. Thus, FIG. 1a shows that using the protocol known from PCT/EP96/03595 an amplification took place only in two of 19 samples tested (samples No. 4 and 15).

Surprisingly, it was found that it was possible to dramatically improve the amplificability of the DNA by replacing the standard buffer with one of buffers E1 to E8 shown in Table 1 below.

TABLE 1

| | Na acetate | NaCl | KCl | EDTA | SDS | PVP-10 | pH |
|---|---|---|---|---|---|---|---|
| E1 | 0.2 M | 2.5 M | — | 60 mM | 1.5% | 2% | 6.5 |
| E2 | 0.2 M | 0.5 M | — | 50 mM | 1.4% | 3% | 5.0 |
| E3 | 0.1 M | 1.0 M | — | 60 mM | 1.0% | 4% | 6.0 |

TABLE 1-continued

| | Na acetate | NaCl | KCl | EDTA | SDS | PVP-10 | pH |
|---|---|---|---|---|---|---|---|
| E4 | 0.1 M | 0.5 M | — | 50 mM | 1.4% | 2% | 5.5 |
| E5 | 0.3 M | — | 0.1 M | 80 mM | 1.5% | 3% | 6.0 |
| E6 | 0.1 M | — | 0.2 M | 50 mM | 1.4% | 2% | 5.5 |
| E7 | 0.3 M | — | 0.5 M | 60 mM | 1.0% | 1% | 4.0 |
| E8 | 0.2 M | — | 0.1 M | 60 mM | 1.0% | 1% | 6.5 |

FIG. 1b shows that it was possible to isolate an amplifiable DNA from all 19 samples when using an extraction buffer of the invention.

EXAMPLE 2

Stool Extraction at Elevated Temperature

For detection of nucleic acids from particular cells (e.g. bacteria, parasites) or viruses, an extraction of the stool sample at elevated temperatures is expedient in order to ensure efficient release of the DNA.

$10^5$ agrobacteria were added to in each case 1 g of stools and worked up according to the method in Example 1. The stool sample was extracted in a buffer of the invention for 5 min at 4° C., room temperature of 18–25° C. (RT), 50° C., 70° C., 80° C. or 90° C. The efficiency of lysis was determined via the total DNA yield and the efficiency of lysis of the added agrobacteria was determined via the amplification of a specific agrobacteria sequence (vir gene). The results are shown below in Table 2.

TABLE 2

| Temperature | Total DNA yield (ng/µl) | Vir amplification |
|---|---|---|
| 4° C. | 115 | + |
| RT | 161 | ++ |
| 50° C. | 255 | +++ |
| 70° C. | 536 | ++++ |
| 80° C. | 521 | +++++ |
| 90° C. | 548 | ++++++ |

The results are based on in each case two independent stool extractions at the temperature indicated. Total DNA yield was determined via OD measurement at 260 nm. The amplification products were fractionated on an agarose gel. + indicates the efficiency of amplification (+ to ++++: increasing efficiency).

Table 2 shows that both total DNA, yield and lysis of bacteria and thus the amplification yield increased markedly when increasing the incubation temperature to at least 50° C., in particular to at least 70° C.

What is claimed is:

1. A method for isolating a nucleic acid from a biological sample comprising the steps of:
   (a) providing an extraction buffer comprising a phenol-neutralizing substance, wherein said extraction buffer
      (i) has a pH from 3 to 7, and
      (ii) has a salt concentration of at least about 100 mM;
   (b) contacting said extraction buffer with a biological sample containing nucleic acid, and contacting said biological sample with an adsorption matrix; and
   (c) isolating said nucleic acid from said adsorption matrix.

2. The method of claim 1, wherein said extraction buffer has a pH from about 4 to about 6.5.

3. The method of claim 1, wherein said extraction buffer comprises at least one salt from the group consisting of KCl and NaCl.

4. The method of claim 1, wherein said phenol-neutralizing substance comprises at least about 0.5% polyvinylpyrrolidone.

5. The method of claim 1, wherein said adsorption matrix comprises an insoluble carbohydrate.

6. The method of claim 5, wherein said adsorption matrix comprises a component of potato flour.

7. The method of claim 1, wherein said biological sample comprises fecal material.

8. The method of claim 1, wherein said extraction buffer is incubated with said biological sample before contacting said extraction buffer and said biological sample with said adsorption matrix.

9. The method of claim 8, wherein said incubation occurs at a temperature of less than or equal to about 10° C.

10. The method of claim 8, wherein said incubation comprises at least one treatment regime selected from the group consisting of chemical treatment, thermal treatment, and enzymatic treatment.

11. The method of claim 8, wherein said incubation occurs at a temperature of greater than or equal to about 50° C.

12. The method of claim 1, wherein contacting said biological sample with said adsorption matrix occurs under at least one physical condition selected from the group consisting of centrifugation, reduced pressure, and gravity.

13. The method of claim 10, wherein contacting said biological sample with said adsorption matrix occurs under at least one physical condition selected from the group consisting of centrifugation, reduced pressure, and gravity.

* * * * *

UNITED STATES PATENT AND TRADEMARK OFFICE
CERTIFICATE OF CORRECTION

PATENT NO.        : 6,992,182 B1
APPLICATION NO.   : 09/889093
DATED             : January 31, 2006
INVENTOR(S)       : Oliver Müller et al.

It is certified that error appears in the above-identified patent and that said Letters Patent is hereby corrected as shown below:

On the Title page of U.S. Pat. No. 6,992,182, in field (73), identify the second Assignee, as follows: Insert;

--Max-Planck-Gesellschaft zur Förderung der Wissenschaften, Munich (DE)--

Signed and Sealed this

Sixth Day of March, 2007

JON W. DUDAS
*Director of the United States Patent and Trademark Office*